United States Patent
John et al.

(10) Patent No.: US 12,396,942 B2
(45) Date of Patent: Aug. 26, 2025

(54) **SEED EXTRACT OF *Annona cherimola***

(71) Applicant: CLR-Chemisches Laboratorium Dr. Kurt Richter GmbH, Berlin (DE)

(72) Inventors: Sabrina John, Berlin (DE); Anne Steinmüller, Berlin (DE); Heiko Prade, Berlin (DE)

(73) Assignee: CLR-Chemisches Laboratorium Dr. Kurt Richter GmbH, Berlin (DE)

( * ) Notice: Subject to any disclaimer, the term of this patent is extended or adjusted under 35 U.S.C. 154(b) by 711 days.

(21) Appl. No.: 17/435,196

(22) PCT Filed: Feb. 27, 2020

(86) PCT No.: PCT/EP2020/055198
§ 371 (c)(1),
(2) Date: Aug. 31, 2021

(87) PCT Pub. No.: WO2020/178147
PCT Pub. Date: Sep. 10, 2020

(65) Prior Publication Data
US 2022/0142909 A1 May 12, 2022

(30) Foreign Application Priority Data
Mar. 1, 2019 (EP) .................................... 19160417

(51) Int. Cl.
*A61K 36/00* (2006.01)
*A61K 8/9789* (2017.01)
*A61Q 19/00* (2006.01)

(52) U.S. Cl.
CPC .......... *A61K 8/9789* (2017.08); *A61Q 19/007* (2013.01)

(58) Field of Classification Search
CPC ..................................................... A61Q 19/00
See application file for complete search history.

(56) References Cited

U.S. PATENT DOCUMENTS

2008/0139518 A1* 6/2008 Purcell .................. A61K 31/07
514/559

FOREIGN PATENT DOCUMENTS

JP   H0912433    1/1997
JP   2006249051  9/2006

OTHER PUBLICATIONS

Garcia-Salas et al., Identification and quantification of phenolic and other polar compounds in the edible part of Annona cherimola and its by-products by HPLC-DAD-ESI-QTOF-MS. Food Research International, (Dec. 2015) vol. 78, pp. 246-257. (Year: 2015).*
Albuquerque et al., Nutritional and phytochemical composition of Annona cherimola Mill. fruits and by-products: Potential health benefits. Food Chemistry, (Feb. 15, 2016) vol. 193, pp. 187-195 (Year: 2016).*
Definition of aqueous from dictionary.com, accessed on Oct. 16, 2024, p. 1 (Year: 2024).*
International Search Report and Written Opinion in corresponding PCT/EP2020/055198, dated Mar. 30, 2020.
Quílez, et al., "Potential therapeutic applications of the genus *Annona*: Local and traditional uses and pharmacology", Journal of Ethnopharmacology, 2018, 225, pp. 244-270.
Amoo, et al., "Compositional Evaluation of *Annona cherimoya* (Custard Apple) Fruit", Trends in Applied Sciences Research, 2008, 3(2), pp. 216-220, http://www.docsdrive.com/pdfs/academicjournals/tasr/2008/216-220.pdf.
Bories, et al., "Antiparasitic Activity of Annona muricata and Annona cherimolia Seeds", Planta Med, 1991, 57(5), pp. 434-436 (abstract attached).
Lozoya, et al., "A uterotonic substance from Annona cherimola seeds", Am J Chin Med. Autumn, 1980, 8(3), pp. 268-270 (abstract attached).
Monteiro Egydio, et al., "Underutilized *Annona* Species from the Brazilian Cerrado and Amazon Rainforest: A Study on Fatty Acids Profile and Yield of Seed Oils", Economic Botany, 2011, 65(329) (abstract attached).
Chemisches Laboratorium, "AnnonaSense CLR—Adaptogenic approach for skin health and well-being", 2019, http://www.lakepersonalcare.co.uk/Whats%20New%20In-Cos/CLR/AnnonaSense%20CLR%20Brochure.pdf.
Anonymous, "Ginger Inflammation & Healing All-in-One Liquid Coconut Oil", GNPD03, 2017, www.gnpd.com, Database accession No. 4580563.
"Botanical Orange Spa Body Gel", MINTEL GNPD, www.gnpd.com/sinatra/recordpage/6109145, Published Nov. 2018 according to MINTEL, Last Retrieved Sep. 27, 2022.
Dweck, "Isoflavones, phytohormones and phytosterols", Journal of Applied Cosmetology, 2006, 24, pp. 17-32.

(Continued)

*Primary Examiner* — Qiuwen Mi
(74) *Attorney, Agent, or Firm* — Hovey Williams LLP; Crissa A. Cook

(57) ABSTRACT

The present invention generally relates to the field of cosmetics. More particularly, the invention relates to a cosmetic skincare composition comprising a seed extract of the plant *Annona cherimola*. The invention is based on the finding that such seed extract has several favourable effects on skin. Amongst others, a seed extract of *Annona cherimola* exerts calming, soothing, moisturizing and anti-itching effect. In another aspect, the invention therefore provides a cosmetic method of improving skin appearance or reducing skin dryness in a subject, comprising administering a skin care composition of the present invention. In yet another aspect, the invention provides a cosmetic method of soothing or calming irritated skin in a subject, comprising administering a skin care composition of the present invention. The invention also relates to the use of a seed extract of *Annona cherimola* for skin care, and in particular for soothing or calming irritated skin, or improving skin appearance or reducing skin dryness and itching.

11 Claims, 4 Drawing Sheets

(56) References Cited

OTHER PUBLICATIONS

"Genomer Repair Hand Cream", MINTEL GNPD, www.gnpd.com/sinatra/recordpage/ 4067633, Published Jun. 2016 according to MINTEL, Last Retrieved Sep. 27, 2022.

"GlamGlow Poutmud Wet Lip Balm", MINTEL GNPD, www.gnpd.com/sinatra/recordpage/5733261, Published Jun. 2018 according to MINTEL, Last Retrieved Sep. 27, 2022.

"Hello Kitty Facial Mask", MINTEL GNPD, www.gnpd.com/sinatra/recordpage/2568061, Published Jul. 2014 according to MINTEL, Last Retrieved Sep. 27, 2022.

Search Report in corresponding Australian application 2020230944 dated Sep. 27, 2022.

\* cited by examiner

SEED EXTRACT OF *Annona cherimola*

RELATED APPLICATIONS

This application is the U.S. National Stage of International Patent Application No. PCT/EP2020/055198, filed Feb. 27, 2020, which is hereby incorporated by reference in its entirety, and which claims priority to European Patent Application No. 19160417.2, filed Mar. 1, 2019.

The present invention generally relates to the field of cosmetics. More particularly, the invention relates to a cosmetic skin care composition comprising a seed extract of the plant *Annona cherimola*. The invention is based on the finding that such seed extract has several favourable effects on skin. Amongst others, a seed extract of *Annona cherimola* exerts calming, soothing, moisturizing and anti-itching effect. In another aspect, the invention therefore provides a cosmetic method of improving skin appearance or reducing skin dryness in a subject, comprising administering a skin care composition of the present invention. In yet another aspect, the invention provides a cosmetic method of soothing or calming irritated skin in a subject, comprising administering a skin care composition of the present invention. The invention also relates to the use of a seed extract of *Annona cherimola* for skin care, and in particular for soothing or calming irritated skin, or improving skin appearance or reducing skin dryness and itching.

BACKGROUND OF THE INVENTION

Cosmetic products for topical application that improve the appearance of skin are strongly in demand. These products shall soften and moisturize the skin in order to delay the signs of stress and aging. In recent years, a number of chemical compounds that were commonly used in cosmetic products have been replaced by natural ingredients, thereby following the consumers' demand for more natural products.

In particular, plant and herbal extracts are now commonly used as additives in cosmetic products, e.g. skin care products. Some plant extracts have been found to exert highly beneficial effects to skin. For example, extracts of Epilobium angustifolium have been found to sooth the skin. Other extracts, such as extracts from *Avena sativa*, are known to relieve the skin from itching and irritation. Extracts of the bark of *Prunus serotina* were found to strongly moisturize the skin. Accordingly, plant or herbal extracts are widely used by the cosmetic industry due to their wide variety of skin improving properties.

Despite the progress that has been made in the field of cosmetics in the past in identifying and developing natural ingredients for skin care products, there is still a need for additional natural ingredients that reduce symptoms of irritated skin, such as itching, dryness and redness.

DISCLOSURE OF THE INVENTION

The present invention is based on the finding that seed extracts obtained from the cherimoya plant (*Annona cherimola*), and preferably aqueous seed extracts, are highly suitable for being used in skin products. Specifically, it has been found by the inventors that seed extracts of *Annona cherimola* are effective in soothing and calming the human skin. In addition, as shown in the examples described herein, seed extracts of *Annona cherimola* enhance the activity of the cannabinoid receptor-2, inhibit the activity of the signal transducer and activator of transcription 3 (STAT3) and inhibit the expression of IL-1β, IL-8 and the calcitonin gene-related peptide (CGRP). Finally, seed extracts of *Annona cherimola* also reduce itching and redness and reduce pain perception of irritated skin.

In a first aspect, the present invention provides a cosmetic skin care composition comprising, as an active ingredient, a seed extract of the plant *Annona cherimola*. The seed extract preferably is an aqueous seed extract. The seed extract will be present in the skin care composition in an amount that is sufficient for inducing at least one of the above-mentioned skin-improving effects. Generally, a skilled person working in the field of cosmetics will be readily able to add the seed extract in suitable amounts to the final skin care composition.

In a preferred embodiment, the seed extract is present in the cosmetic skin care composition in an amount of 0.05 to 25.0% (w/w). This means that the seed extract can be present in the cosmetic skin care composition in a range from about 0.05 to about 25.0% (w/w), from about 0.05 to about 20.0% (w/w), from about 0.05 to about 15.0% (w/w), from about 0.05 to about 10.0% (w/w), from about 0.05 to about 8.0% (w/w), from about 0.1 to about 25.0% (w/w), from about 0.1 to about 20.0% (w/w), from about 0.1 to about 15.0% (w/w), from about 0.1 to about 10.0% (w/w), from about 0.1 to about 8.0% (w/w), from about 0.5 to about 25.0% (w/w), from about 0.5 to about 20.0% (w/w), from about 0.5 to about 15.0% (w/w), from about 0.5 to about 10.0% (w/w), from about 0.5 to about 8.0% (w/w), from about 0.1 to about 20.0% (w/w), from about 0.5 to about 15.0% (w/w), from about 1.0 to about 10.0% (w/w), from about 1.0 to about 8.0% (w/w), from about 2.0 to about 25.0% (w/w), from about 2.0 to about 20.0% (w/w), from about 2.0 to about 15.0% (w/w), from about 2.0 to about 10.0% (w/w), from about 2.0 to about 8.0% (w/w), from about 3.0 to about 25.0% (w/w), from about 3.0 to about 20.0% (w/w), from about 3.0 to about 15.0% (w/w), from about 3.0 to about 10.0% (w/w), from about 3.0 to about 8.0% (w/w), from about 4.0 to about 25.0% (w/w), from about 4.0 to about 20.0% (w/w), from about 4.0 to about 15.0% (w/w), from about 4.0 to about 10.0% (w/w), or from about 4.0 to about 8.0% (w/w). In a most preferred embodiment, the seed extract is present in the cosmetic composition in an amount of about 0.5% to 3% (w/w).

As used herein, the term "plant extract" refers to a blend of compounds isolated from a plant. A plant extract may be prepared from one or more part of the plant, e.g., the whole plant, the flower, the seed, the fruit or the leaves of the plant. Accordingly, the term "seed extract" refers to a blend of compounds isolated from the seed of a plant. The extract can be obtained by incubation of seed material with a solvent following standard procedures described in the art. The term encompasses crude extracts as well as extracts that have been subjected to one or more enrichment or purification procedure. The seed extract of the invention may be present in liquid form, preferably as a solution, or in solid form, such as in dried powder.

A seed extract can be prepared on the basis from *Annona cherimola* seeds that have been removed from fruits of the plant. For preparing the seeds, the fruits are opened and the fruit pulp is removed. The seeds may then be dried before further processing. Drying may be carried out at a temperature of between 20° C. and 80° C., preferably between 25° C. and 70° C. and most preferably between 30° C. to 50° C. A drying temperature of 40° C. is particularly preferred. The weight loss that occurs by drying should be in the range from 1% to 20% (w/w), preferably from 2.5% to 12% (w/w), and more preferably from 5% to 10%.

Before disintegration, the plant material can be blanched at temperatures between 45° C. and 100° C., to eliminate bacterial contamination and improve the digestion quality. Furthermore, blanching reduces the activity of enzymes such as hydrolases, lipases and oxidases, thereby increasing the stability and quality of the plant material.

The seeds are then disintegrated prior to contacting them with the solvent. Disintegration can be effected, for example, by repeated freezing and thawing, or by suitable devices such as homogenizers, high-pressure homogenizers or ultrasonic homogenizers, mills, or grinders. For example, a standard ball mill or French press can be used. The seeds may be disintegrated in frozen or non-frozen form. In addition, the decomposition of the cells of the seed material may also be achieved enzymatically. To this end, the seeds may be dehulled and treated with appropriate enzymes that lead to the destruction of the structural components of the cells. Incubation of the seed material with pectinase, collagenase, cellulase and/or hemicellulases is suitable to effectively decompose the cell.

In the next step, the disintegrated seed material is contacted with a suitable solvent for extraction. Suitable solvents for extraction are water, aqueous buffers, such phosphate buffered saline or citrate buffer, glycols, such as propylene glycol, or butylene glycol, or glycol-water mixtures, alcohols or alcohol-water mixtures, in particular ethanol or ethanol-water mixtures, or methanol or methanol-water mixtures, glycerin or glycerin-water mixtures.

It will be preferred that the seed extract used in the preparation of the skin care composition of the invention is an aqueous seed extract, i.e. an extract prepared with an aqueous solvent, preferably water or an aqueous buffer. This has a particular advantage that the extracts will not comprise significant amounts of acetogenins. Briefly, acetogenins are a class of polyketides found in plants of the Annonaceae family. To date, more than 400 acetogenins are known, many of which neurotoxic. Acetogenins are hardly soluble in water and will therefore not accumulate in an aqueous extract. If seed extracts are prepared with organic solvents, acetogenins have to be removed from the extract before formulating them into skin care products.

In a preferred embodiment, an aqueous seed extract is used in the skin care composition of the invention which comprises no or only a small amount of acetogenins. As a result, the cosmetic skin care composition of the invention preferably comprises less than 0.001% (w/w), and more preferably less than 0.0001% (w/w), and even more preferably less than 0.00001% (w/w) acetogenins. In a particularly preferred embodiment, the skin care composition of the invention is free of acetogenins.

In another preferred embodiment, an aqueous seed extract is used in the skin care composition of the invention which comprises no or only a small amount of phytosterols. As a result, the cosmetic skin care composition of the invention preferably comprises less than 0.001% (w/w), and more preferably less than 0.0001% (w/w), and even more preferably less than 0.00001% (w/w) phytosterols. In a particularly preferred embodiment, the cosmetic skin care composition of the invention is free of phytosterols.

A mass spectrometry analysis of an extract prepared in accordance with the below examples revealed that it contains cherimolacyclopeptides A, B, C, D, E and F as well as the alkaloids isoboldine, reticuline, corydine, michelalbine, and riboflavin. Therefore, in another preferred embodiment, an aqueous seed extract is used in the cosmetic skin care composition of the invention which comprises at least one peptide selected from the group of cherimolacyclopeptides A, B, C, D, E and F. More preferably, an aqueous seed extract is used which comprises cherimolacyclopeptides A-F. In yet another preferred embodiment, an aqueous seed extract is used in the cosmetic skin care composition of the invention which comprises at least one alkaloid selected from the group of isoboldine, reticuline, corydine, michelalbine, and riboflavin. More preferably, an aqueous seed extract is used which comprises all of these alkaloids.

In a preferred embodiment, the solvent is water. In another preferred embodiment, the solvent is a sodium-citrate buffer according to Soerensen, for example, a buffer containing 0.1 M disodium citrate and 0.1 N HCl having pH between 1.2 and 5.0, preferably between 2.0 and 5.0, such as pH 3.0. In another preferred embodiment, the solvent is a sodium-citrate buffer according to Soerensen, for example, a buffer containing 0.1 M citric acid monohydrate ($C_6H_8O_7 \times H_2O$) and 0.1 M trisodium citrate dihydrate solution having a pH of 5.0. In yet another preferred embodiment, the solvent is a phosphate buffer according to Soerensen, for example, a buffer containing 0.06 M potassium phosphate and 0.06 M disodium phosphate, having a pH of between 5 and 8, such as pH 5. The ratio of seed material-to-solvent during extraction can be in the range of 1:100 (w/w) to 50:100 (w/w). Preferably, the ratio of seed material-to-solvent during extraction is 5:100 (w/w) or more, 10:100 (w/w) or more, 15:100 (w/w) or more, 20:100 (w/w) or more, 25:100 (w/w) or more, 30:100 (w/w) or more, 35:100 (w/w) or more, 40:100 (w/w) or more, 45:100 (w/w) or more, or 50:100 (w/w).

After extraction the liquid phase is separated from solid plant material, e.g. by decanting, centrifugation, filtration or a combination of these methods. For example, a standard decanter device can be used, such as the CA 22 device (GEA Westfalia Separator Group GmbH, Oelde, Germany). The extraction mixture resulting from the decanter can be subjected to an additional filtration step, such as membrane filtration. The liquid phase obtained in this manner is considered as the abstract according to the invention.

The extract can be directly used for formulating the skin care composition of the invention. It is however preferred to keep the extract for several hours at ambient temperature for 1-24 hours, preferably for 8-16 hours in order to stabilize the extract. The extract may then be subjected to filtration another time to remove any residual solids. For this purpose, a 0.2 μm celluloseacetate membrane may be used.

The cosmetic skin care composition of the invention is preferably formulated for topical application which means that the composition is provided in a form that allows the consumer to dispense the composition after application to the skin. Preferably, the skin care composition of the invention is formulated as a liquid, ointment, cream, scrub, lotion, paste, gel, hydrogel, foam, or powder. Where the composition is formulated as a liquid, it can be packaged into a pump dispenser which allows spraying the liquid onto the skin areas to be treated. The skin care composition of the invention can also be incorporated into a patch which is applied to the skin.

In a particular preferred embodiment the composition of the invention is formulated for topical application to the skin of the subject. The skin to be treated may include the skin of the face and the body, e.g. the skin of the neck, chest, back, arms, hands, legs or thighs. According to a preferred embodiment, the skin to be treated with the composition of the present invention is the skin of the face. According to another preferred embodiment, the skin to be treated with the composition of the present invention is the skin of the body.

The skin care compositions may be applied to the area of skin in need of treatment, e.g. the face or body, at least once a day, twice a day, or even more frequently if needed. When applied twice daily, the first and second applications are preferably separated by at least 6 hours, preferably 8 hours. Typically, the cosmetic composition is applied once in the morning and once in the evening. The composition of the invention can be used over long periods without any adverse side effects. For example, the period of treatment may be at least 1 week, at least 2 weeks, at least 3 weeks, at least 4 weeks, at least 6 weeks, at least 12 weeks, at least 24 weeks, or more. In some embodiments, the treatment will be extended for several months, such as for 4 months, 6 months, 8 months, 12 months, 18 months, or 24 months.

Apart from the seed extract, the skin care composition of the invention will comprise at least one dermatologically acceptable carrier. The carrier may be present in the skin care composition in an amount of about 30% to about 99%, preferably from about 40% to about 98%, more preferably from about 50% to about 97%, more preferably from about 60% to about 96%, and even more preferably from about 70% to about 95%, by weight of the skin care composition of the invention. As used herein, a dermatologically acceptable carrier is compatible both with the skin and the other ingredients in the composition. In particular, a dermatologically acceptable carrier will not irritate or otherwise affect the skin adversely. Also, a dermatologically acceptable carrier will not interfere with the activity or solubility or dispersibility of other ingredients in the composition. Suitable dermatologically acceptable carriers include, but are not limited to, aqueous solutions, emulsions, dispersions, and solids. In a preferred embodiment, the dermatologically acceptable carrier is an emulsion. The emulsion may be oil-in-water emulsion, a water-in-oil emulsion, or a water-in-oil-in-water emulsion. When an emulsion is used as a carrier, it is preferred that the aqueous phase of the emulsion comprises the *Annona cherimola* seed extract. The emulsion may contain one or more anionic, cationic or non-ionic emulsifier, e.g., in an amount of 1% to about 5% based on the weight of the carrier.

The composition of the invention may further comprise additional optional ingredients that are commonly used in cosmetic skin care products. Such ingredients are described in great detail, for example, in the International Cosmetic Ingredient Dictionary and Handbook, 16$^{th}$ ed. (2016). For example, the composition of the invention may also include one or more of the following: antioxidants, binders, pH adjusters, buffering agents, colorants, thickeners, emollients, humectants, exfoliating agents, preservatives, plant extracts, essential oils, and fragrances.

For example, the composition of the invention may comprise an exfoliating compound such as urea. Exfoliating compounds which are useful in the compositions of the present invention include, but are not limited to, urea, alpha-hydroxy acids and beta-hydroxy acids, and their esters, anhydrides, and salts. Suitable hydroxy acids include, for example, urea, glycolic acid, lactic acid, malic acid, mandelic acid, tartaric acid, citric acid, 2-hydroxyalkanoic acid, salicylic acid, and derivatives thereof. The use of urea is particularly preferred, because it also has an additional water-binding effect and enhances the absorption of other cosmetic ingredients. The skin care composition of the invention may comprise from about 1% to about 5% (w/w) of the exfoliating compound. In some embodiments, the composition may contain two or more different exfoliating compounds.

In one preferred embodiment, the skin care composition of the present invention comprises a compound that serves as a pH adjuster. Since the composition of the invention is used on the human skin, it will normally have a slightly acidic pH to make it more compatible with the acidic environment of the skin. The composition may have a pH in the range from about 2.5 to about 6.5, preferably from about 4.0 to about 6.0, and more preferably from about 5.0 to about 6.0 or from about 5.5 to about 6.0. The acidic pH can be achieved by adding an acid to the skin care composition of the invention, e.g. a carboxylic acid, such as an alpha hydroxy acid. The nature of the acid that can be used in the composition of the invention is not particularly limited. Suitable acids include formic acid, acetic acid, propionic acid, butyric acid, valeric acid, caproic acid, enanthic acid, caprylic acid, and the like. In a particular preferred embodiment, the composition comprises lactic acid as a pH adjuster. For application to the human skin, lactic acid is particularly useful, as it is also secreted by the skin flora to form the protective acidic milieu on the human skin surface.

The skin care composition of the present invention may also comprise an emollient. Suitable emollients for the skin care composition of the present invention include, but are not limited to, olive oil, palm oil, soybean oil, sesame seed oil, rapeseed oil, evening primrose oil, sunflower seed oil, avocado oil, olive oil, coconut oil, castor oil, safflower seed oil, myristyl lactate, isopropyl myristate, polyethylene glycol, isopropyl palmitate, isopropyl stearate, isobutyl palmitate, isocetyl stearate, or cetyl alcohol. The skin care composition of the invention may comprise from about 1% to about 5% (w/w) of the emollient. In some embodiments, the composition may contain two or more different emollients.

The skin care composition of the present invention may also comprise a humectant for improving skin hydration. Suitable humectants for use in the composition of the present invention include, but are not limited to, glycerine, polyethylene glycol ethers of glycerine, amino acids, such as proline and arginine, sugar and sugar alcohols, such as glucose, mannose, trehalose, and polyglycerol sorbitol, 1,3-butylene glycol, propylene glycol, diglycerol, glycerol monopropoxylate, glycogen, sodium hyaluronate, sodium poly-aspartate, sodium polyglutamate, sorbeth 20, sorbeth 6, and hydrogenated starch hydrolysates. The skin care composition of the invention may comprise from about 1% to about 5% (w/w) of the humectant. In some embodiments, the composition may contain two or more different humectants.

It is preferred that the skin care composition of the present invention comprises at least about 30% (w/w) water. More preferably, the skin care composition comprises at least about 35% (w/w) water, at least about 40% (w/w) water, at least about 45% (w/w) water, at least about 50% (w/w) water, at least about 55% (w/w) water, at least about 60% (w/w) water, at least about 65% (w/w) water, at least about 70% (w/w) water, at least about 75% (w/w) water, at least about 80% (w/w) water, at least about 85% (w/w) water, or at least about 90% (w/w) water. An amount of at least about 70% (w/w) water in the final skin care composition is most preferred.

In another aspect, the present invention provides a cosmetic method of improving skin appearance in a subject, comprising administering a composition as described elsewhere herein to the skin of said subject. In yet another aspect, the present invention provides a cosmetic method of reducing skin dryness in a subject, comprising administering a composition as described elsewhere herein to the skin of said subject. In yet another aspect, the present invention provides a cosmetic method of soothing irritated skin, comprising administering a composition as described elsewhere herein to the skin of said subject. In yet another aspect, the present invention provides a cosmetic method of calming irritated skin, comprising administering a composition as described elsewhere herein to the skin of said subject. In a particular preferred embodiment, the above methods comprise the topical administration of the composition to the facial skin. In another particular preferred embodiment, the above cosmetic methods achieve the desired effect by one or more of the following activities: agonizing the cannabinoid receptor-2, enhancing the activity of the cannabinoid receptor-2, inhibiting or reducing the activity of the signal transducer and activator of transcription 3 (STAT3), inhibiting the expression of IL-1β, inhibiting the expression of IL-8, inhibiting the expression of the calcitonin gene-related peptide (CGRP).

In another aspect, the present invention provides for the use of a composition as described elsewhere herein, i.e. a composition comprising a seed extract of *Annona cherimola* as an active ingredient, for cosmetic skin care. Specifically, the composition is used for soothing irritated skin, calming irritated skin, improving skin appearance and/or reducing skin dryness and itching. Preferably, the above use of seed extract is based on one or more of the following activities: agonizing the cannabinoid receptor-2, enhancing the activity of the cannabinoid receptor-2, inhibiting or reducing the activity of the signal transducer and activator of transcription 3 (STAT3), inhibiting the expression of IL-1β, inhibiting the expression of IL-8, inhibiting the expression of the calcitonin gene-related peptide (CGRP).

As used herein, all percentages are by weight of the cosmetic skin care composition, unless specifically stated otherwise. All ratios are weight ratios, unless stated otherwise.

EXAMPLES

Figure 1:
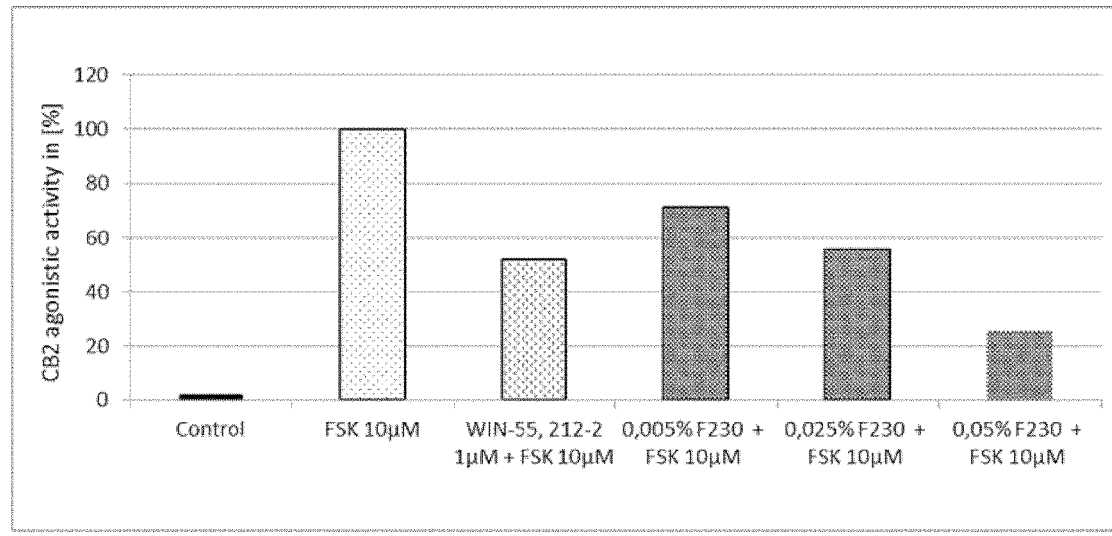
FIG. 1 shows that the extract F230 acts as a cannabinoid receptor-2 agonist. 293T-CB2-CRE-luc cells were treated with the extract F230 or the positive control WIN-55,212-2 for 15 min. Subsequently, cells were incubated with 10 µM Forskolin. After six hours incubation, the cells were lysed and luciferase activity was measured. The specific transactivation observed for F230 is expressed as [%] of Forskolin stimulation.

The following examples describe certain preferred embodiments of the present invention. It is however to be noted that the invention is not limited to such embodiments.

Example 1: Preparation of *Annona cherimola* Seed Extract

Extracts of *Annona cherimola* were prepared as follows. Fruits from *Annona cherimola* were opened and the fruit pulp was removed. The seeds were harvested and subjected to drying overnight at a temperature of 40° C. After drying, seeds were disintegrated by milling. The disintegrated seeds were then extracted for 4 h at 50° C. using a sodium-citrate buffer comprising 0.1 M citric acid monohydrate ($C_6H_8O_7 \cdot H_2O$) and 0.1 M trisodium citrate, dihydrate $C_6H_5O_7Na_3 \cdot 2H_2O$), pH 6.0.

After extraction, the liquid phase was separated from solid plant material using a decanter CA 22 device (Westfalia Seperator AG). The liquid fraction was kept for 16 hours at room temperature for stabilization and subsequently subjected to a final filtration step using a 0.2 µm celluloseacetate membrane. The extract so obtained is referred to as "F230" in the following. Mass spectrometry analysis of the extract F230 revealed that it contains cherimolacyclopeptides A, B, C, D, E and F (see references 1-10) as well as alkaloids isoboldine, reticuline, corydine, michelalbine, and riboflavin.

Example 2: Cannabinoid Receptor-2 Agonistic Activity

The cannabinoid receptor 2 (CB2) is part of a complex regulation system that is involved in inflammation. Amongst others, the activity of this receptor is involved in thermo-regulation, cell growth, host defense, apoptosis, pruritus, pain, and wound healing (Soethoudt et al. (2017), Nat. Commun. 8, 13958; Ibsen (2017), Cannabis and Cannabinoid Research 2:1, 48-60). The activation of CB2 leads to suppression of inflammatory cytokines and pain inducing neuropeptides like substance CGRP (Calcitonin Gene-Related Peptide). Therefore, compounds that enhance the activity of CB2 are potentially useful for mitigating inflammatory states of the skin that are associated, for example, with atopic dermatitis, psoriasis and pruritus.

For assessing the potential effect of an F230 extract prepared as described in Example 1, 293T-CB2 cells which had been stably transfected with cDNA encoding the human cannabinoid receptor 2 (CB2) were incubated in 24-well plates at a density of $1 \times 10^5$ cells/ml and transiently transfected with 0.1 µg/ml of the plasmid CRE-luc containing six consensus cAMP responsive elements (CRE) linked to firefly luciferase. Transient transfection was performed with Rotifect (Carl Roth GmbH, Karlsruhe, Germany) according to the manufacturer's instructions. Cells were harvested 24 h after transfection.

To measure the CB2 agonistic activity of F230, 293T-CB2-CRE-luc cells were treated either with increasing concentrations of the F230 extract or the positive control WIN-55,212-2 (Sigma Aldrich, Taufkirchen, Germany) for 15 min and then with 10 µM Forskolin (Sigma Aldrich, Taufkirchen, Germany). After six hours of stimulation, the cells were lysed in 25 mM Tris-phosphate pH 7.8, 8 mM $MgCl_2$, 1 mM DTT, 1% Triton X-100, and 7% glycerol. The luciferase activity was then measured using an Autolumat LB 9501 (Berthold Technologies, Bad Wildbad, Germany) following the instructions of the luciferase assay kit (Promega, Madison, USA). The background obtained with the lysis buffer was subtracted in each experiment, and the specific transactivation was expressed as [%] of Forskolin stimulation (the latter of which was set to 100%).

Results: The results are depicted in FIG. 1. The assay results reflect a CB2 agonist activity as inhibition of Forskolin-induced CRE-Luc activity. It can be seen that the positive control WIN-55,212-2 acts as a CB2 agonist and partially antagonizes the effect of Forskolin. The same effect is also observed for F230, whereas the level of Forskolin antagonization increases with increasing amounts of F230. Consequently, the assay demonstrates that F230 exerts a CB2 agonistic activity.

Example 3: STAT3 Inhibition Activity

The signal transducer and activator of transcription 3 (STAT3) is a human transcription factor encoded by the STAT3 gene. STAT3. During skin inflammation, IFN-γ stimulates the expression of STAT3 which in turn induces the expression of additional proinflammtory cytokines, thereby contributing to inflammation (Archer et al. (2017), The Journal of Immunology, 198 (1 Supplement) 197.4). The inhibition of IFN-γ-stimulated STAT3 expression is thought to reduce an inflammatory immune response of the skin.

For assessing the potential effect of an F230 extract prepared as described in Example 1 on STAT3 activity, HeLa-STAT3-luc cells that had been stably transfected with the plasmid 4×M67 pTATA TK-Luc were used. The cells were seeded at a density of $2×10^4$ cells/ml in 96-well plates the day before the assay. Then the cells were treated with F230 for 15 min and subsequently stimulated with 25 U/ml IFN-γ.

After 6 h the cells were washed twice with phosphate buffered saline (PBS) and lysed by incubation in 50 µl lysis buffer containing 25 mM Tris-phosphate (pH 7.8), 8 mM $MgCl_2$, 1 mM DTT, 1% Triton X-100 (Sigma Aldrich, Taufkirchen, Germany), and 7% glycerol (Sigma Aldrich, Taufkirchen, Germany) for 15 min at RT in a horizontal shaker.

Luciferase activity was measured using a plate reader Berthold/LB 941 (Berthold Technologies) following the instructions of the luciferase assay kit (Promega, Madison, WI, USA). The relative luminescence unit (RLU) was calculated and the results expressed as percentage of inhibition of STAT3 activity induced by IFN-γ (100% activation). The experiments for each concentration of the test items were done in triplicate wells.

Figure 2:
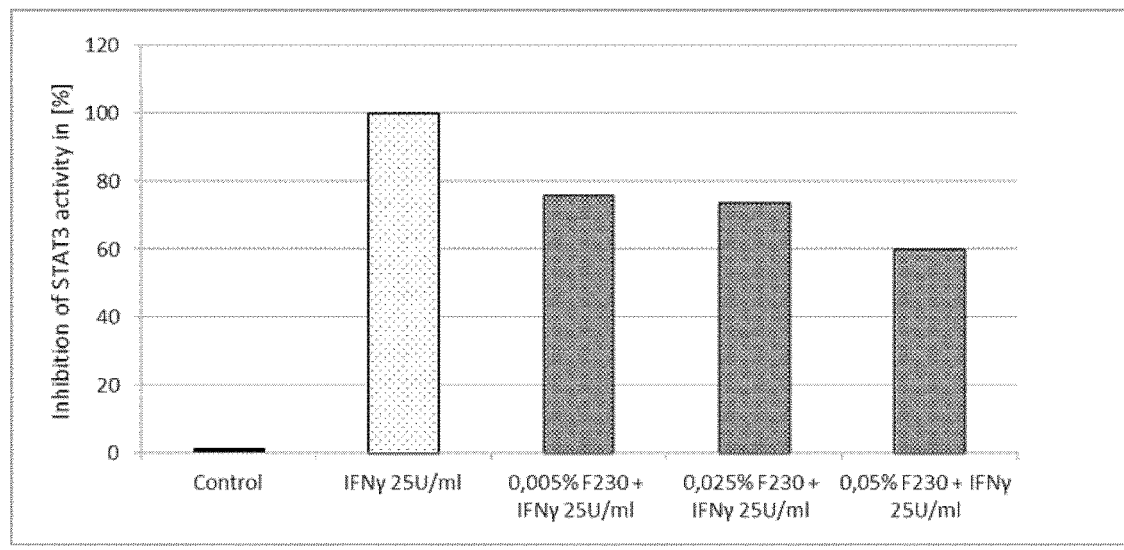
FIG. 2 shows that the extract F230 has a STAT3-inhibiting activity. HeLa-STAT3-luc cells were treated with F230 and stimulated with IFN-γ. After 6 h the cells were lysed and the luciferase activity was measured. The results are expressed as percentage of the inhibition of STAT3 activity induced by IFN-γ (100% activation). The experiments for each F230 concentration were made in triplicate.

Results: The results are depicted in FIG. 2. As can be seen from the figure, F230 counteracts the IFN-γ-induced STAT3 activity. Increasing amounts of F230 result in higher levels of STAT3 inhibition.

Example 4: Inhibition of IL-1β and IL-8 Expression

As pro-inflammatory cytokines, IL-1β and IL-8 are involved in numerous skin diseases that are associated with inflammation, such as psoriasis, atopic dermatitis, neutrophilic dermatoses, and eczema (Jensen (2010); Current opinion in investigational drugs (London, England: 2000); 11(11), 1211-20); Bou-Dargham et al. (2017), Med. Res. Rev., 37: 180-216; Amarbayasgalan et al. (2013), Int Arch Allergy Immunol, 160:63-74). Accordingly, inhibition of the production of these cytokines is helpful for mitigating skin inflammation.

To examine whether an F230 extract prepared as described in Example 1 is able to inhibit IL-1β and IL-8 expression, a co-culture system of keratinocytes and human sensory neurons was used. Human sensory neurons were derived from human induced pluripotent stem cells (hiPS cells). hiPS cells were obtained by transfecting human fibroblasts which were reprogrammed into neuronal cells. hiPS cells were plated in 6 wells plates coated by a thin layer of Matrigel® (Corning GmbH, Kaiserslautern, Germany) at a density of 250,000 cells in a medium composed by DMEM-F12 (Pan-Biotech, Aidenbach, Germany) supplemented with 10% Knockout Serum Replacement (Life technologies, Carlsbad, USA), 0.1 µM retinoic acid (Sigma Aldrich, Taufkirchen, Germany), 1% P/S (Pan-Biotech) and a cocktail of inhibitors. The culture was maintained for 6 days at 37° C. and 5% of $CO_2$.

After 6 days of differentiation, hiPS cells were plated at a density of 20,000 cells in the differentiation medium using 96-well plates that had been coated with a thin layer of Matrigel®. After 9 days, the culture medium was replaced by a maturation medium, i.e. a DMEM-F12 supplemented with 1% N2 (Life technologies, Carlsbad, USA), 10 ng/mL Neurotrophin-3 (NT-3), 10 ng/mL glial cell-derived neurotrophic factor (GDNF, Pan-Biotech), 10 ng/mL of brain-derived neurotrophic factor (BDNF, PanBiotech) and 10 ng/mL Nerve Growth Factor (NGF, Sigma). Commercial human keratinocytes were thawed and propagated in 75 $cm^2$ culture flasks in keratinocyte growth medium. At the end of propagation, the cells were dissociated and frozen in liquid nitrogen. At day 14 of the neuronal culture, keratinocytes were thawed again and plated in 96-well plates on top of the neurons at the density of 30,000 cells per well in a medium composed by ⅔ of maturation medium and ⅓ of keratinocyte growth medium. The medium was changed every 2 or 3 days. On day 18, the medium was removed and fresh medium was added, either (i) control medium, or (ii) medium containing capsaicine, or (iii) medium containing capsaicine and capsazepine, or (iv) medium containing capsaicine and F230 in 3 different concentrations. After 1 hour of capsaicin stimulation, supernatants were removed and assayed for cytokine release. Samples were evaluated by cytometry flux (BD Bioscience) and compared to non-treated controls.

Figure 3:
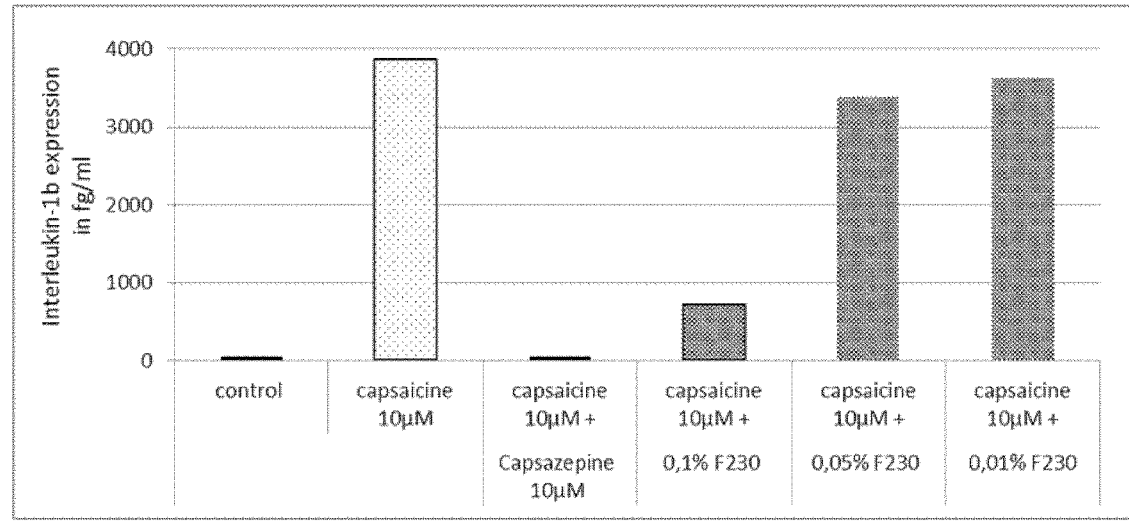
FIG. 3 shows that the extract F230 effectively reduces the capsaicine-induced release of the cytokine IL-1β in a co-culture of keratinocytes and human sensory neurons.
Figure 4:
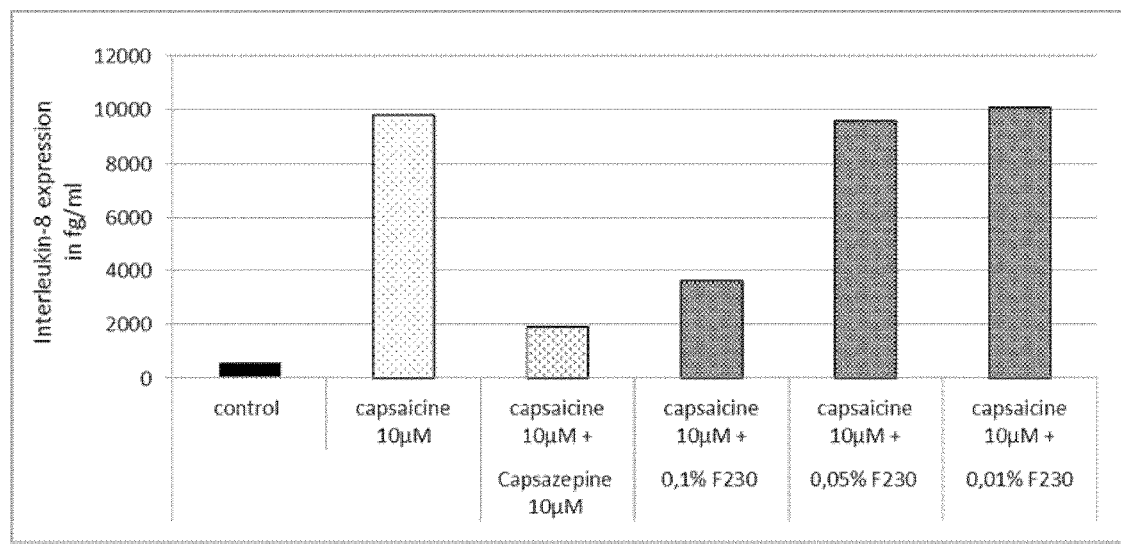
FIG. 4 shows that the extract F230 effectively reduces the capsaicine-induced release of the cytokine IL-8 in a co-culture of keratinocytes and human sensory neurons.

Results: The results of measuring IL-1β secretion are depicted in FIG. 3. Incubation with capsaicine strongly induced IL-1β expression. To the contrary, a treatment of the co-cultured cells with capsazepine before or during cell activation with capsaicin completely abrogates IL-1β release. Similarly, increasing amounts of F230 resulted in increasing levels of inhibition of IL-1β expression. The results of measuring IL-8 secretion are depicted in FIG. 4. Incubation with capsaicine strongly induced IL-8 expression, while treatment of the co-culture with capsazepine before or during cell activation with capsaicin significantly reduced IL-8 release. Similarly, increasing amounts of F230 resulted in increasing levels of inhibition of IL-8 expression.

Example 5: Inhibition of CGRP

The calcitonin gene-related peptide (CGRP) is a member of the calcitonin family of peptides that acts as a neuropeptide. The release of CGRP is associated with neurogenic inflammation by blood vessel dilatation resulting in erythema and pain. CGRP production is induced by capsaicine. The above-described co-culturing approach with human sensory neurons and keratinocytes was used to measure the amount of CGRP released into the supernatant after 30 minutes of stimulation with 10 µM capsaicine. For CGRP detection, an ELISA (Antibodies-online) was used. The results obtained were compared to non-treated cells.

Figure 5:
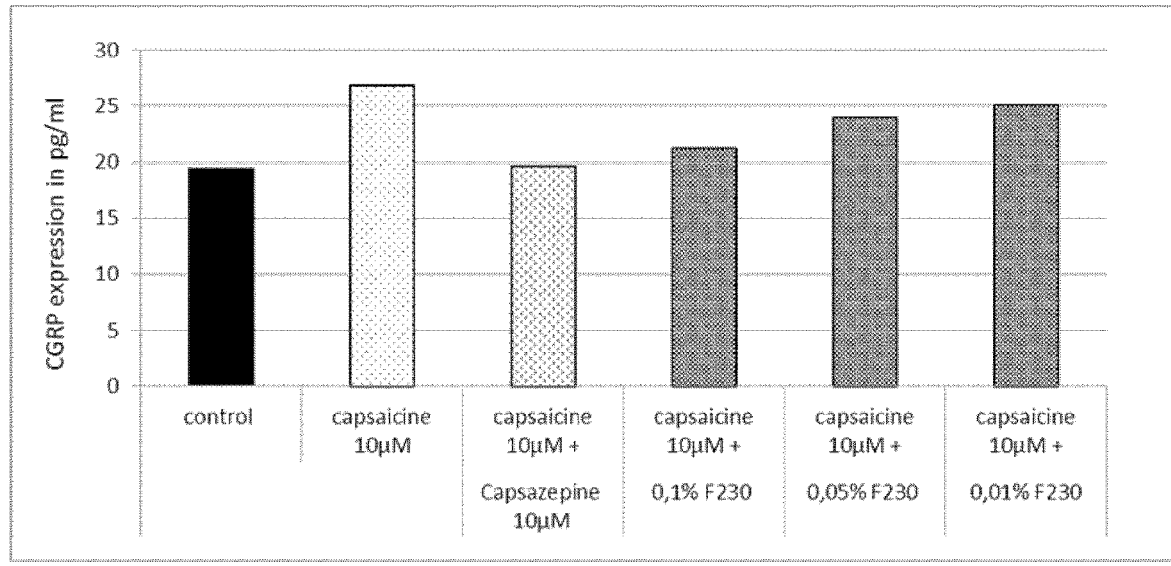
FIG. 5 shows that the extract F230 reduces capsaicine-induced CGRP expression. Increasing amounts of F230 result in higher levels of CGRP expression inhibition.

Results: The results are depicted in FIG. 5. As can be seen from the figure, F230 counteracts the capsaicine-induced CGRP expression. Increasing amounts of F230 result in higher levels of CGRP expression inhibition.

Example 6: Reduction of Skin Itching

For in-vivo studies a composition containing F230 and a placebo composition were prepared.

The composition with 3% F230 was prepared as follows:
A. Deionized water 237.875 g
B. Xanthan gum 2.50 g
C. Euxyl PE9010 2.00 g
D. F230 7.5
E. Citric acid (10%) 0.125 g Components A and B are mixed and dispersed to homogeneity. Subsequently, components C-E are added in the given order. Finally, the pH is adjusted to 5.71.

The placebo composition was prepared as follows:
A. Deionized water 238.00 g
B. Xanthan gum 2.50 g
C. Euxyl PE9010 2.00 g
D. Deionized water 7.50 g Components A and B are mixed and dispersed to homogeneity. Subsequently, components C-D are added in the given order. The pH of the composition was adjusted to 5.70.

To examine the effect of F230 on skin itching, the composition containing 3% F230 was applied to itching skin. A double blind study with 42 healthy volunteers was conducted (9 males and 33 females). 22 volunteers were assigned to F230 treatment, and 20 volunteers were assigned to placebo treatment. Some of the volunteers had a history of dry and itchy skin, including 11 subjects with atopic dermatitis, 8 subjects with type IV allergy, 1 subject with psoriasis, and 1 subject with diabetes type II. 12 volunteers had sensitive skin. 9 volunteers had normal skin. Itching was scored at the time points t=0, 1 min, 5 min and 24 hours. The baseline at t=0 was set to 0%. The frequency of itching was assessed by the test subjects on a 5-point scale before and after use of the test compositions.

Figure 6:
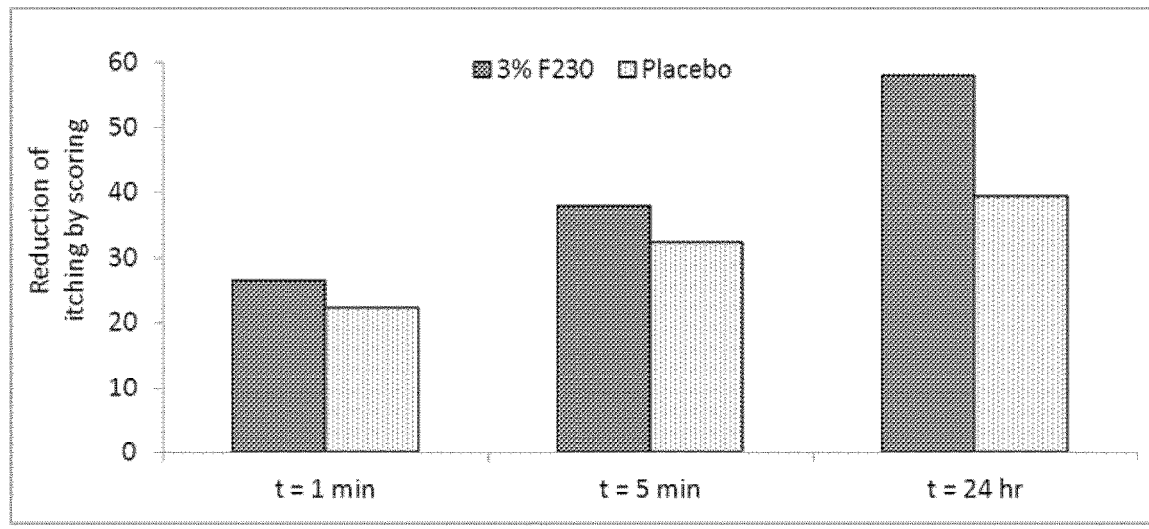
FIG. 6 shows that the extract F230 reduces skin itching significantly compared to placebo already 1 minute after application.

Results: The results are depicted in FIG. 6. It can be seen that itching was significantly reduced by F230 compared to placebo already 1 minute after application.

Example 7: Reduction of Skin Redness

To examine the effect of F230 on skin redness, a formulation containing 3% F230 was applied to skin with abnormal redness. The volunteers used in Example 6 were used for the study. The formulation was applied twice daily. Redness was scored at t=0 and after 17 days of application. The baseline at t=0 was set to 0%. Before and after the test period, a trained grader evaluated any erythema that occurred at the skin of a subject due to scratching.

Figure 7:
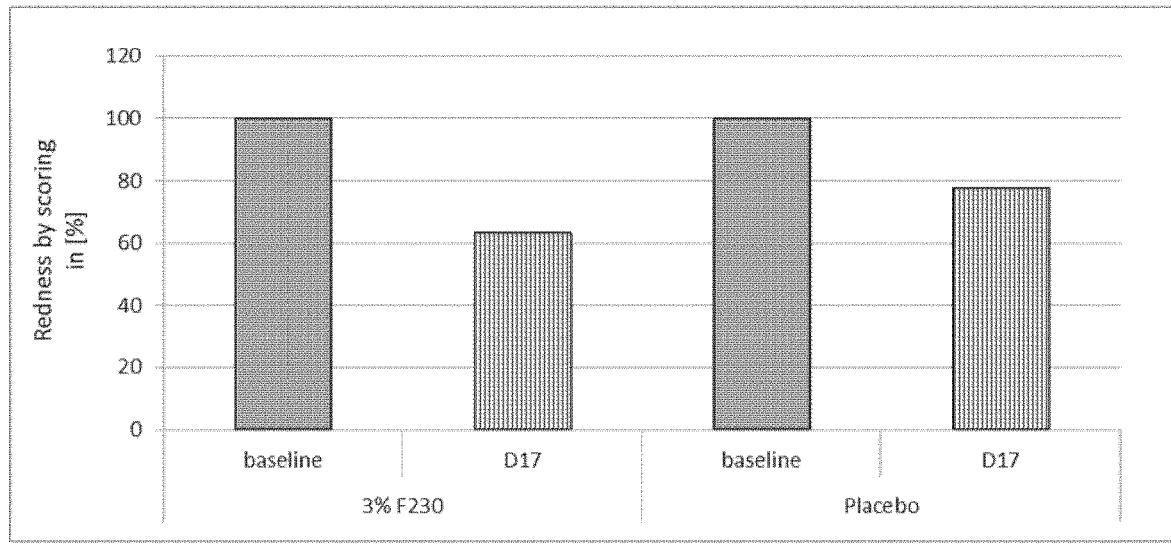
FIG. 7 shows that the extract F230 reduces skin redness significantly compared to placebo 17 days after application.

Results: The results are depicted in FIG. 7. It can be seen that the redness due to scratching was reduced by F230 compared to placebo after two weeks of application (Day 17) compared to baseline (Day 1).

Example 8: Reduction of Skin Sensitivity

To examine a neurosoothing effect of F230 on skin sensitivity, a formulation containing 3% F230 was applied to skin. The volunteers used in Example 6 were used for the study. The formulation was applied one time. The skin sensitivity was determined by measuring the current perception threshold (CPT) with a Neurometer® CPT/C device (Neurotron Inc., Baltimore, USA) at 250 HZ and 5 Hz at t=0 (i.e. immediately before application) and 40 min after application of test formulations or placebo. The baseline at t=0 was set to 0%.

Figure 8:
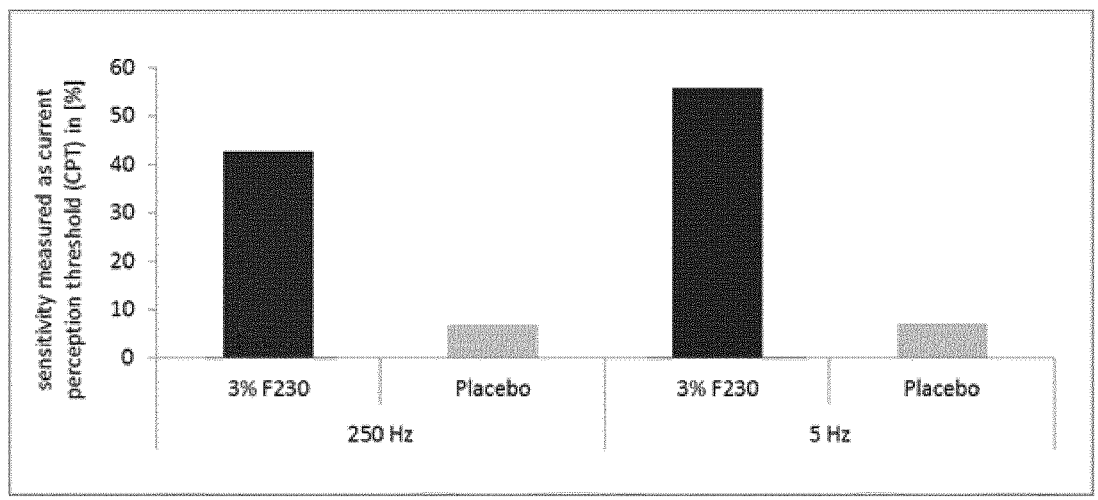
FIG. 8 shows that the extract F230 increases the perception threshold of the skin compared to placebo.

Results: The results are depicted in FIG. 8. It can be seen that both at 250 Hz and at 5 Hz, the perception threshold is much higher after treatment of the skin with F230 compared to placebo.

REFERENCE LIST

1) Li C.-M., et al. (1997), Phytochemistry, 45, 521-523,
2) Li C.-M., et al. (1998), Phytochemistry, 47, 1293-1296,
3) Li C.-M., et al. (1998), Phytochemistry, 48, 555-556,
4) Li C.-M., et al. (1997), Phytochemistry, 50, 1047-1052,
5) Morita H., et al. (1999), Tetrahedron, 55, 7509-7518,
6) Wélé A., et al. (2005), Phytochemistry, 66, 1154-1157,
7) Wélé A., et al. (2002), Tetrahedron, 60, 405-414,
8) Wélé A., et al. (2004), J. Natural Prod., 67, 1577-1579,
9) Wélé A., et al. (2005), Phytochemistry, 66, 693-696,
10) Wélé A., et al. (2005), Phytochemistry, 66, 2376-2380.

The invention claimed is:

1. A cosmetic skin care composition comprising a seed extract of the plant *Annona cherimola*, wherein the extract is a water extract, and wherein the extract is present in the composition in an amount of 0.05 to 25.0% (w/w), and wherein said composition comprises less than 0.001% (w/w) acetogenins.

2. The cosmetic skin care composition according to claim 1, wherein said composition is formulated for topical application.

3. The cosmetic skin care composition of claim 2, wherein the said composition is formulated for topical application to the skin of the face or body.

4. The cosmetic skin care composition according to claim 1, wherein said composition is formulated as an ointment, cream, lotion, paste, gel, hydrogel, foam or powder.

5. The cosmetic skin care composition according to claim 1, wherein said composition comprises an emollient selected from the group consisting of olive oil, palm oil, soybean oil, sesame seed oil, rapeseed oil, evening primrose oil, sunflower seed oil, avocado oil, olive oil, coconut oil, castor oil, safflower seed oil, myristyl lactate, isopropyl myristate, polyethylene glycol, isopropyl palmitate, isopropyl stearate, isobutyl palmitate, isocetyl stearate, and cetyl alcohol.

6. The cosmetic skin care composition according to claim 1, wherein said composition has a pH in the range from about 2.5 to about 6.5.

7. The cosmetic skin care composition according to claim 1, wherein said composition comprises a humectant selected from the group consisting of glycerine, polyethylene glycol ethers of glycerine, amino acids, sugar and sugar alcohols, 1,3-butylene glycol, propylene glycol, diglycerol, glycerol monopropoxylate, glycogen, sodium hyaluronate, sodium poly-aspartate, sodium polyglutamate, sorbeth 20, sorbeth 6, and hydrogenated starch hydrolysates.

8. The cosmetic skin care composition according to claim 1, wherein said composition comprises an exfoliating compound selected from the group consisting of urea, alpha-hydroxy acids and beta-hydroxy acids, and their esters, anhydrides, and salts.

9. A cosmetic method of improving skin appearance or reducing skin dryness in a subject, comprising administering a composition of claim 1 to the skin of said subject.

10. A cosmetic method of soothing or calming irritated skin in a subject, comprising administering a composition of claim 1 to the skin of said subject.

11. A cosmetic method of claim 9, wherein said administration comprises topical administration to the skin of the face or body of said subject.

\* \* \* \* \*